United States Patent [19]
Glatz et al.

[11] Patent Number: 5,614,154
[45] Date of Patent: Mar. 25, 1997

[54] CONNECTING CAPILLARY

[75] Inventors: Bernd Glatz, Leonberg; Bernhard Dehmer, Rastatt, both of Germany

[73] Assignee: Hewlett-Packard Company, Palo Alto, Calif.

[21] Appl. No.: 511,560

[22] Filed: Aug. 4, 1995

[30] Foreign Application Priority Data

Aug. 23, 1994 [DE] Germany .............................. 9413553 U

[51] Int. Cl.⁶ .................................................. B01L 11/00
[52] U.S. Cl. ............................................. 422/103; 422/99
[58] Field of Search ........................................ 422/103, 99

[56] References Cited

U.S. PATENT DOCUMENTS

| | | | |
|---|---|---|---|
| 4,293,415 | 10/1981 | Bente, III et al. | 210/198.2 |
| 4,593,691 | 6/1986 | Lindstrom et al. | 128/303.14 |
| 4,988,975 | 1/1991 | Nap | 340/450.3 |
| 5,205,154 | 4/1993 | Lee et al. | 73/23.35 |
| 5,223,226 | 6/1993 | Wittmer et al. | 422/100 |
| 5,268,103 | 12/1993 | Jameson et al. | 210/634 |
| 5,289,003 | 2/1994 | Musser | 250/288 |
| 5,298,225 | 3/1994 | Higdon | 422/89 |
| 5,358,612 | 10/1994 | Dasgupta et al. | 204/108.1 |
| 5,389,221 | 2/1995 | Jorgenson et al. | 204/299 R |
| 5,444,208 | 8/1995 | Mortensen | 219/121.48 |

FOREIGN PATENT DOCUMENTS

| | | |
|---|---|---|
| 0460409A3 | 12/1991 | European Pat. Off. . |
| 0636882A1 | 2/1995 | European Pat. Off. . |
| 2654835 | 5/1991 | France . |
| 4112258A1 | 10/1992 | Germany . |
| 9405378 U | 3/1994 | Germany . |
| 9413553 U | 8/1994 | Germany . |
| WO89/07759 | 2/1989 | United Kingdom . |
| 2238257 | 11/1990 | United Kingdom . |
| WO93/24952 | 12/1993 | WIPO . |
| 9324952 | 12/1993 | WIPO . |

OTHER PUBLICATIONS

EPO Search Report dated Dec. 1, 1995.
German PTO Search Report.
Dallas et al. "Direct chrometographic comparison of the relative adsorption activity of various types of capillary transfer tubing", Analytica Chimica Acta, 251 (1991) 83–93.

*Primary Examiner*—Jill Warden
*Assistant Examiner*—Sharidan Carrillo

[57] ABSTRACT

A connecting capillary for analytical measuring-technology, in particular for high pressure liquid chromatography and for capillary electrophoresis, comprises a glass capillary, in particular a fused silica capillary, which is characterized in that the glass capillary is surrounded at least it its end regions by a sheath of polyetheretherketone (PEEK) or a PEEK-derivative.

3 Claims, 3 Drawing Sheets

CONNECTING CAPILLARY

FIELD OF THE INVENTION

The invention relates to a connecting capillary for analytical measurement technology, in particular for high-pressure liquid chromatography and for capillary electrophoresis. Connecting capillaries of this kind are needed in order to connect various components of an analytical measuring device, for example a liquid chromatograph or a capillary electrophoresis device, to each other.

BACKGROUND OF THE INVENTION

In liquid chromatography, when using separation columns with diameters smaller than approximately 2 mm, connecting capillaries having an inner diameter of 50–100 micrometers are required. Such connecting capillaries are, for example, arranged between the sample injector of the liquid chromatograph and the separation column, or between the exit of the separation column and the detector. The connecting capillaries have to have the mentioned small inner diameters in order to maintain the separation performance of the column.

When using separation columns with larger inner diameters one usually employs steel capillaries as connecting capillaries. With the previously mentioned small diameters, however, steel capillaries can no longer be used, since their inner roughness and the non-constant diameter quickly lead to clogging. It is known to use capillaries made of fused silica for the mentioned small diameters. Fused silica capillaries are also used in gas chromatography or capillary electrophoresis as separation columns. These fused silica capillaries can be manufactured with constant diameter and smooth inner surface in the mentioned diameters of approximately 50 to 100 micrometers.

Connecting capillaries of fused silica for high-pressure liquid chromatography with inner diameters of 50 or 100 micrometers and with an outer diameter of 1/16 inch (1.6 mm) and with the corresponding 1/16 inch fitting are commercially available. The known connecting capillaries are coated on their outside with aluminum, and above this is a coating of fluorinated polymers, for example PVDF. Such connecting capillaries, however, have proved in practical tests not to be satisfactory. On the one hand, the coat of PVDF tends to irreversibly withdraw, thus leaving a dead volume in the fitting region, which deforms the peak form of the chromatographic peak and thus substantially reduces the separation performance of the column. On the other hand, the capillary is pushed out of the fitting during extended operation and when using conventional fittings.

In view of the prior art it is an object of the invention to provide a connecting capillary for analytical measurment technology which has a small and substantially constant inner diameter, a smooth inner wall, and which can be equipped with a fitting in an easy way, and which does not have the previously mentioned disadvantages. In particular, it is to be avoided by the invention that additional dead volume is introduced in the fitting region, even if the fitting is in use for a longer period.

SUMMARY OF THE INVENTION

According to the invention, these objects are solved by claim 1.

The invention is based on the surprising finding that, by using glass capillaries, in particular fused silica capillaries, which are surrounded at least in their end regions by a coat of polyetheretherketone (PEEK) or a PEEK-derivative, a plurality of advantageous effects can be achieved. The capillaries according to the invention are resistant against the solvents typically used in analytical measurement technology, furthermore they are chemically inert against acids and salts, for example sodium chloride and there are, for example for the analysis of proteins, no unwanted interactions with the capillary material, as is the case when using steel capillaries (bio-compatibility). Furthermore, there are excellent dispersion properties relative to commercially available capillaries. In addition, the danger of clogging is small despite of a small inner diameter. Due to the PEEK coat, the mechanical robustness of the capillary is increased, an efficient protection against breaking or scratching of the capillary is achieved. Furthermore, a connecting capillary according to the invention is compatible with conventional fittings used in analytical measurement technology, and a connecting capillary according to the invention can be manufactured with integrated fitting made of PEEK. While a conventional fitting consists of several individual parts, all parts in a fitting according to the invention are combined into a single part, except for an external nut. The fitting according to the invention ensures a stable and permanent connection over a long period of time. Finally the invention permits to manufacture connecting capillaries at a very low cost.

The connecting capillary according to the invention can either be designed as an endless capillary which is completely covered on its outside with PEEK, or the PEEK-coat can only be provided in the end regions of the capillary. In the latter case the regions of the capillary where there is no PEEK-coat can be surrounded by a shrinkable plastic tube. In that way an additional protection against scratches is achieved.

In a preferred embodiment of the invention the glass capillary is a fused silica capillary; however, other materials can also be used, for example a boron silicate glass. Preferred inner diameters for the glass capillaries are 50–150 micrometers, but it is in principle possible to use diameters in the region of approximately 5–1000 micrometers. Fused silica capillaries for example are easy to manufacture with such diameters.

DETAILED DESCRIPTION OF THE INVENTION

In the following, embodiments of the invention will be explained with reference to the drawing.

Figure 1:
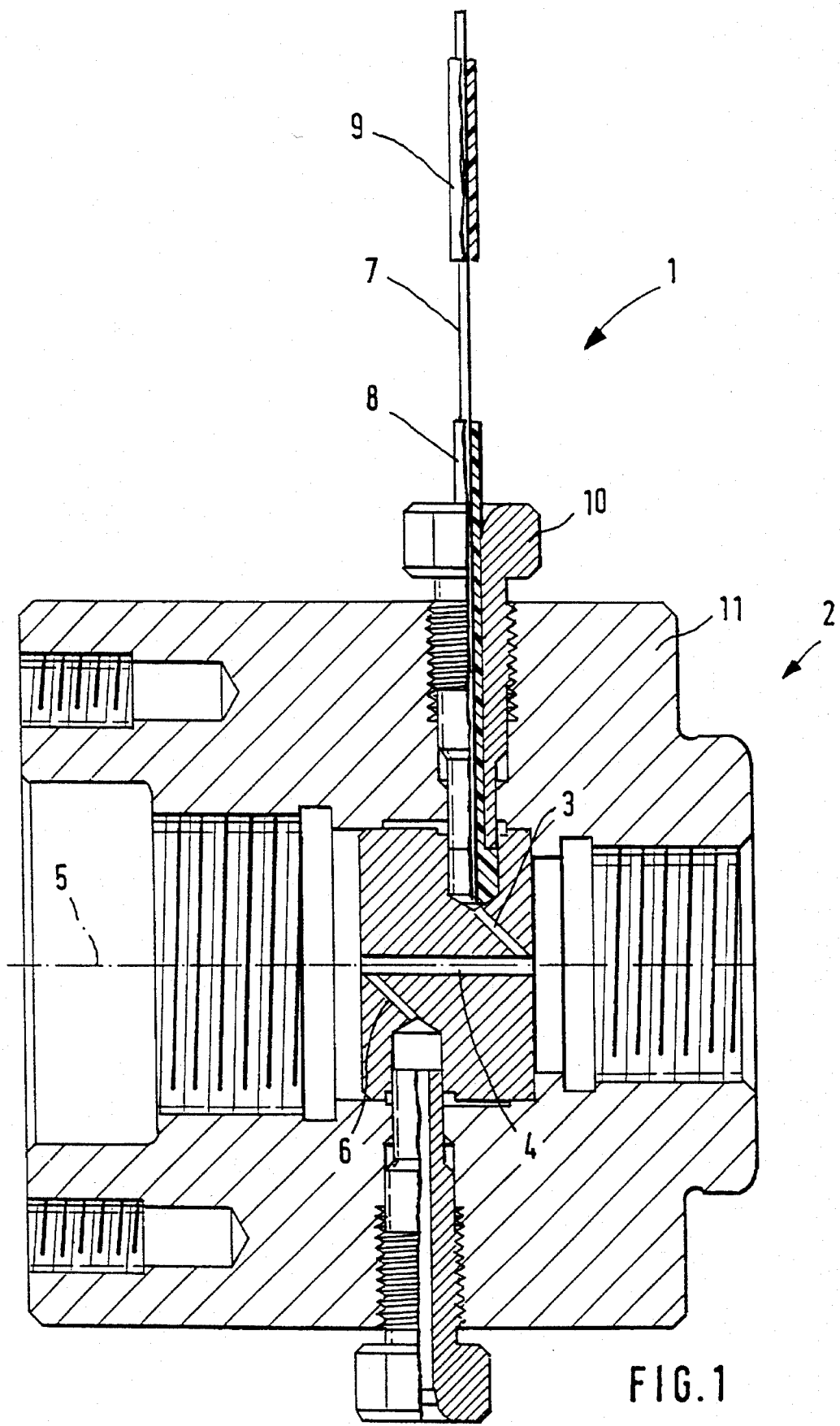
FIG. 1 shows a first embodiment of the invention in connection with a special detector fitting in liquid chromatography.

FIG. 1 shows a connecting capillary 1 according to the invention which is connected to a detector 2 of a liquid chromatograph. With the help of the detector 2 sample substances are detected which exit from the chromatographic column in time succession. These substances are transported into a detector channel 4 through the connecting capillary 1 and an inlet channel 3. The detector channel 4 is irradiated by a light beam along an optical axis 5. This light beam is attenuated in a way which is characteristic for the sample. The attenuated light beam is detected by a light-sensitive sensor (not shown). The sample flows out of the detector channel 4 via an outlet channel 6.

The connecting capillary 1 comprises a stabilized capillary 7 of fused silica; the stabilization is achieved by a coating of polyimide. The end region of the capillary 7 on the detector side is covered by a coat 8 of PEEK (polyetheretherketone). Details of this coat 8 of PEEK are shown in a magnified view FIGS. 2 and 2(a). The coat 8 comprises an enlarged head portion 12 with a chamfer which fits into a corresponding recess of the detector 1 when inserted therein. FIG. 3 shows in detail how the head portion 12 fits into the corresponding recess of the detector. The liquid to be analyzed flows into the inlet channel 3 of the detector through the fused silica capillary 7 arranged in the interior of the coat 8.

The PEEK-coat 8 and the fused silica capillary 7 arranged therein are guided in the interior of a fitting screw 10. The fitting screw 10 has an external thread by means of which it can be screwed into the detector block 11. At the outlet side of the detector there is a fitting of the same kind as on the inlet side. Preferably the fused silica capillary 7 outside the end region is additionally covered by a protective coat 9 of a shrinkable plastic tube which ensures additional protection of the fused silica capillary against scratching and breaking. The shrink tube 9 is shrunk on the capillary 7 by heat treatment; it may consist, for example, of PVDF.

Figure 4:
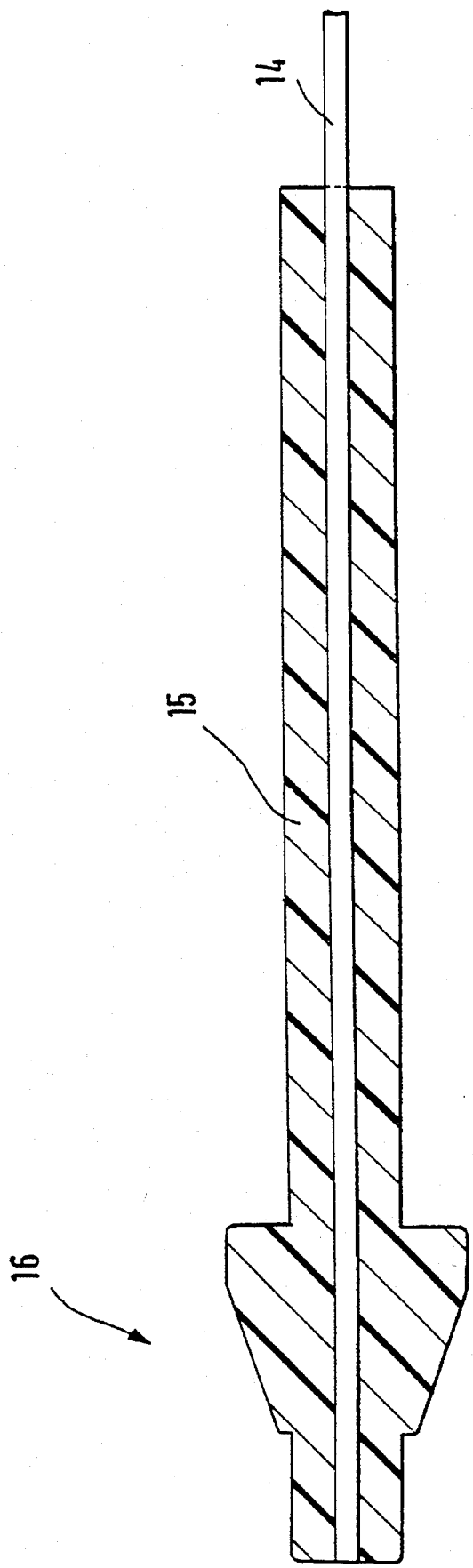
FIG. 4 shows a second, preferred embodiment of the invention.

In FIG. 4, a second, preferred embodiment of the invention is shown wherein the connecting capillary is provided with an integrated fitting. The fused silica capillary 14 is arranged in the interior of the coat 15 which consists of PEEK. The head portion 16 of the PEEK-coat is designed such that it fits into a corresponding counterpart of a 1/16 inch standard fitting usually used in liquid chromatography. For connection with such a counterpart, only a nut (not shown) is required which is pushed over the PEEK coat 15 (right of the head portion 16) and is screwed together with the corresponding threaded piece of a counterpart of the fitting.

In that way, a fitting is provided which has less individual parts than a conventional fitting and which ensures the previously mentioned advantages in the sealing region, for example resistance against solvents and lack of dead volume. The counterpart to the fitting shown in FIG. 4 may of course also be made of PEEK.

Figure 2:
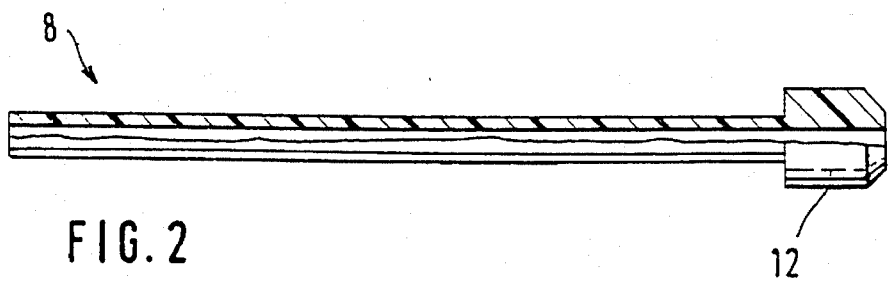
FIG. 2 is a magnified representation of a part of the connecting capillary shown in FIG. 1.
Figure 3:
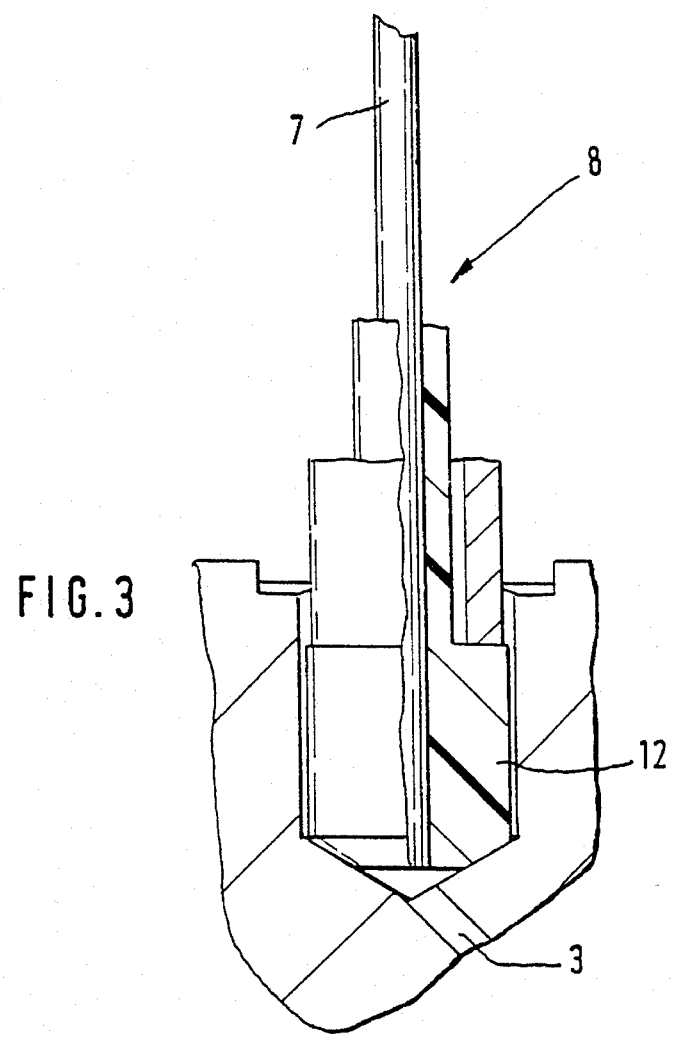
FIG. 3 is a magnified representation of a detail of FIG. 1 in the connecting region between capillary and detector.
Figure 2A:
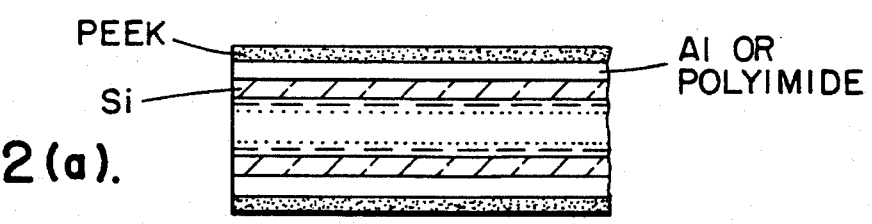
FIG. 2(a) is a section of the capillary of FIG. 2 showing coatings thereon.

The connection between the fused silica capillary and the PEEK pieces shown in FIGS. 2 or 4 can be achieved in different ways. According to a preferred embodiment a stabilized fused silica capillary coated with polyimide or aluminum is injection-molded with PEEK. For this purpose the capillary is fixed in a tool, and then liquid PEEK is cast into a corresponding mold.

The invention provides substantial improvements with regard to dispersion and long-term stability of the pressure drop. In a practical test, when using capillaries with an inner diameter of 75 micrometers between the various components of a liquid chromatograph (seat-injection valve-separation column-detector), no change of the separation performance was detected, whereas, when using conventional steel capillaries with 120 micrometers diameter, a loss of plate number of 40% for a peak of k'=0.3 occurred.

For testing pressure stability a capillary of 1 m length with a 75 micrometer inner diameter was pumped with water in a circle, cyclically with 40° centigrade and 70° eentigrade and 350 bar counter pressure. After a couple of days a clouding of the solvent container due to algae growth could be detected. Nevertheless, the pressure remained constant over the entire period. A comparable 120 micrometer steel capillary would be irreversibly clogged already after a short time.

According to a further aspect of the invention one can also manufacture endless capillaries which are compatible with conventional fittings (for example 1/16 inch fittings) and which can be cut in any length. For this purpose fused silica capillaries coated with polyimide are covered with a PEEK coat in an extrusion process. Typically the fused silica capillaries have a diameter of 350 micrometers and the PEEK-coat is 625 micrometers thick.

We claim:

1. A connecting capillary for an analytical measuring instrument for transferring liquid from one part of the instrument to another part with substantially no interaction between a wall of said capillary and said liquid, said connecting capillary comprising:

a glass capillary having a coated outer surface, a first end and a second end, said coated outer surface consisting of a layer selected from polyimide or aluminum, wherein said layer coats the glass capillary from substantially said first end to said second end;

a unitary, uninterrupted layer of polyetheretherketone (PEEK) or a PEEK derivative in intimate sealing contact with the entirety of said coated outer surface from substantially said first end to said second end of said capillary; and a coupling region at said first end or said second end of said capillary, for attachment of said first end or said second end to said analytical measuring instrument, said coupling region enabling at least a portion of said first end or second end of said capillary to be in contact with a liquid entering or leaving said capillary, said intimate sealing contact between said PEEK or PEEK derivative and said outer surface preventing entry of said liquid therebetween.

2. The connecting capillary as recited in claim 1 wherein said coupling region includes an interconnecting fitting which is formed as an integral, part of said layer of PEEK or PEEK derivative.

3. The connecting capillary as recited in claim 1, wherein said capillary has an inner diameter of approximately 50 to 150 micrometers, and said layer of PEEK exhibits a thickness of approximately 625 micrometers.

* * * * *